United States Patent [19]

Thompson et al.

[11] Patent Number: 4,520,825

[45] Date of Patent: Jun. 4, 1985

[54] DIGITAL CIRCUIT FOR CONTROL OF GRADUAL TURN-ON OF ELECTRICAL TISSUE STIMULATORS

[75] Inventors: David L. Thompson, Fridley; Glenn M. Roline, Anoka; Richard J. Harrington, Roseville, all of Minn.

[73] Assignee: Medtronic, Inc., Minneapolis, Minn.

[21] Appl. No.: 373,679

[22] Filed: Apr. 30, 1982

[51] Int. Cl.³ .............................................. A61N 1/36
[52] U.S. Cl. ................................................... 128/422
[58] Field of Search ................. 128/419 PG, 419 PT, 128/421, 422, 423 R, 419 C, 419 E; 604/20

[56] References Cited

U.S. PATENT DOCUMENTS

| | | | |
|---|---|---|---|
| 3,645,267 | 2/1972 | Hagfors | 128/421 |
| 3,805,796 | 4/1974 | Terry, Jr. et al. | 128/421 X |
| 3,865,119 | 2/1975 | Svensson et al. | 128/419 PT |
| 3,945,387 | 3/1976 | Adams | 128/419 PG |
| 3,983,881 | 10/1976 | Wickham | 128/421 |
| 4,024,875 | 5/1977 | Putzke | 128/419 PG |
| 4,049,004 | 9/1977 | Walters | 128/419 PG |
| 4,066,086 | 1/1978 | Alferness et al. | 128/421 |
| 4,237,899 | 12/1980 | Hagfors et al. | 128/422 |

FOREIGN PATENT DOCUMENTS 0033747  8/1981  European Pat. Off.

Primary Examiner—Lee S. Cohen
Attorney, Agent, or Firm—Merchant, Gould, Smith, Edell, Welter & Schmidt

[57] ABSTRACT

A circuit for causing the gradual turn-on of electrical tissue stimulation in a digitally controlled stimulator is disclosed. A stimulation pulse counter and a pulses per step memory circuit are connected to a decoder to provide an amplitude incrementing signal after a presettable count of stimulation pulses. An amplitude counter receives the incrementing signal to increment the amplitude of the stimulation output pulse through a digital to analog converter circuit and to reset the pulse counter. A maximum amplitude memory circuit and decoder operate in conjunction with the amplitude counter to latch the counter when a preset pulse amplitude is obtained. At the end of a stimulation interval, the amplitude counter is reset and stimulation pulses begin at the minimum amplitude at the start of the next stimulation interval.

7 Claims, 5 Drawing Figures

DIGITAL CIRCUIT FOR CONTROL OF GRADUAL TURN-ON OF ELECTRICAL TISSUE STIMULATORS

FIELD OF THE INVENTION

The invention pertains to the field of electrical tissue stimulators, used in the field of medicine for the treatment of pain. In particular, the invention pertains to digital control circuitry for providing adjustable, gradual increases in the intensity or amplitude of stimulation pulses delivered by an electrical tissue stimulator.

BACKGROUND OF THE PRIOR ART

Tissue stimulators have gained wide acceptance in the field of medicine for the treatment of chronic, intractable pain. Generally, tissue stimulators include electrical circuits for generating electrical stimulation pulses, electrodes for attaching to the affected part of the body, and leads for conveying the stimulation pulses from the generating circuits to the electrodes. In some cases the entire tissue stimulator system is intended to be implanted within the body while in other cases the pulse generating circuitry is contained in a package externally of the body. In the case of transcutaneous stimulators, electrodes having a significant surface area are held in contact with the skin by adhesives or other means over the affected areas. Another type of stimulation which can be used either with external or implanted pulse generators uses leads extending to an implanted electrode, for example one implanted along the spinal cord. In any case, the application of the electrical stimulation pulses to body tissue produces the effect of relieving or masking the sensation of pain. In more sophisticated units, controls or programming may be provided to adjust parameters of the output stimulation such as pulse amplitude and repetition rate. Many tissue stimulator pulse generators also provide a burst or cycle mode wherein groups of individual stimulating pulses are provided at intervals, with delay intervals between the groups.

It is very desirable to provide some means of control over the amplitude or intensity of the stimulating pulses so that the patient using the device can adjust the amplitude for maximum effectiveness. If the amplitude is too low, there may be insufficient relief; and if the amplitude is too high, there can be an unpleasant stinging or tingling sensation. The optimum amplitude changes according to a variety of operating conditions including the length of time the stimulation has been on. Problems have been encountered in burst or cycle mode stimulation wherein the unpleasant stinging or tingling sensation sometimes accompanies the stimulation.

Circuits have been devised in the prior art for providing a gradual increase in the amplitude of pulses within a group of pulses in a burst mode to alleviate this problem. Circuits have utilized resistance-capacitance charging or discharging characteristics to provide a gradual increase in amplitude of the first several pulses within a group leading up to the final pulse amplitude. While this technique has helped in alleviating unwanted tingling sensation, it is subject to the disadvantage of lack of adaptability to different increase rates or slopes and different final pulse amplitudes. Further, resistance-capacitance charging circuits can lead to somewhat higher electrical consumption which may be a major consideration in the case of fully self contained, implantable pulse generator.

SUMMARY OF THE INVENTION

To overcome these and other problems, this invention provides improved circuitry for the control of electrical pulse generation in a tissue stimulator system. The invention is particularly adapted to implantable tissue stimulators, but is also usable in external stimulators. The invention provides digital circuitry which controls the gradual turn-on or increase in pulse amplitude of the initial pulses within a group or burst of output pulses. The invention provides programmability so that the slope or effective rate of increase can be selected by remote programming, as well as the final full amplitude output pulse value. This permits optimum control over pulse characteristics for the most effective pain relief for the patient, and convenient adjustment to new output pulse parameters as it becomes necessary or desirable from time to time.

DETAILED DESCRIPTION OF THE PREFERRED EMBODIMENT

Figure 1:
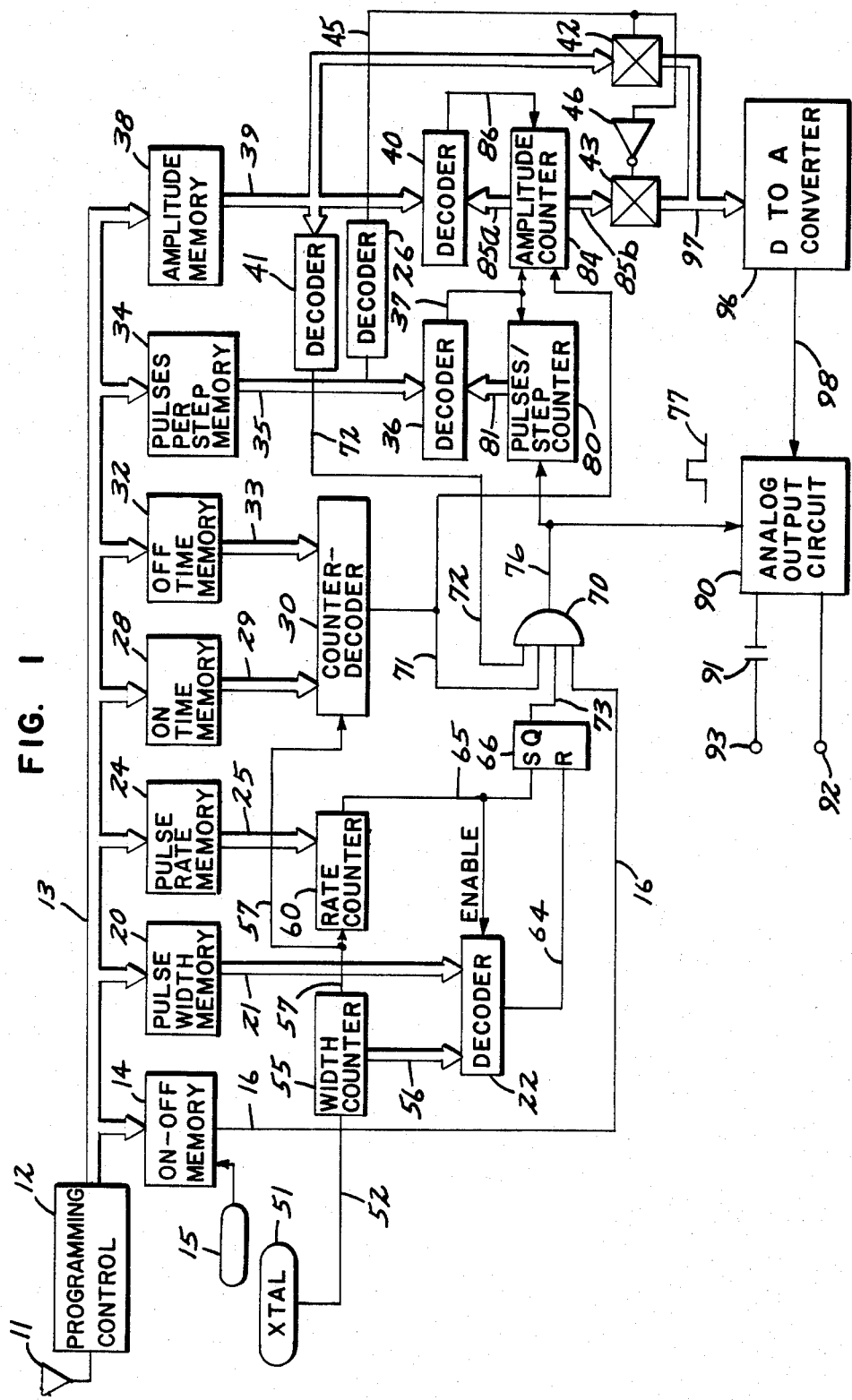
FIG. 1 is an electrical block diagram of a programmable tissue stimulator including the present invention.

The programmable tissue stimulator shown in block diagram in FIG. 1 is intended to be fully implantable, and therefore, the programming takes place by means of coded programming signals transmitted from without the body, and received by suitable receiving and decoding circuitry within the implanted stimulator. The coded programming signals are received by antenna 11 and programming control circuit 12, which includes a receiver, control circuitry therefor, and decoding circuits. Control circuit 12 checks the validity of received signals, decodes them and applies them over data bus network 13 to the various parameter memories as explained more fully below. Various types of systems are known in the art for transmission, reception and decoding of programming signals in implanted devices, and therefore, the circuitry in control 12 is not shown in detail. This invention is preferably used with the particular type of programming signal receiver and control therefor set forth in the commonly assigned copending application Ser. No. 373,798 for "Circuit for Controlling a Receiver in an Implanted Device" by Peter Berntson, filed Apr. 30, 1982, although other types of programming receivers and controls could also be used.

Data bus network 13 is provided for transmitting the program information from control 12 to the various mode memories, and data bus 13 may take the form of serial or parallel data paths as is generally known, and suitable addressing techniques are used in conjunction with data bus network 13 to ensure that the appropriate programming information is transmitted to the correct memory.

ON-OFF memory 14 is connected to data bus network 13 for receiving programming signals indicative of the selected status of the stimulator, i.e. on or off. In addition, a magnetic reed switch 15 is provided within the device and is also connected to memory 14. Reed switch 15 is actuated in the conventional manner by placing an external magnet over the site where the unit is implanted. The status of memory 14 and hence the on or off status of the stimulator can be controlled either by external programming signals or by applying the magnet externally over the site of the implanted stimulator. The status of memory 14 is outputted over conductor 16 which extends to control logic which is explained more fully below.

Pulse width memory 20 comprises a counter or registers for receiving and storing digital data corresponding to the selected pulse width. The count or contents of memory 20 is applied by data bus 21 to an input of a decoder network 22.

Pulse rate memory 24 consists of a counter or registers connected to data bus network 13 to receive and store digital data corresponding to the selected pulse rate. The data content of memory 24 is applied over data bus 25 to an input of counter 60, discussed further below.

ON time memory 28 and OFF time memory 32 are provided for controlling the delivery of stimulation pulses as explained further below. Both memories 28 and 32 are in communication with data bus network 13. These memories consist of counters or registers for receiving and storing digital data corresponding to the desired on and off times, respectively, for the stimulator when in a burst or cycle mode. The data content of memory 28 is applied by data bus 29 to a counter-decoder 30 which also receives the output of memory 32 from data bus 33. Continuous operation occurs when the ON time memory 28 is set to zero.

Memory 34 is another memory or set of registers connected to data bus network 13 for receiving and storing digital data corresponding to the selected number of pulses per step, which corresponds to the slope of the gradual turn-on as explained more fully below. Memory 34 also serves as an on-off control for gradual turn-on operation. The data content of this memory is conveyed over data bus 35 to a decoder 36.

Amplitude memory 38 is another memory or set of registers connected to data bus network 13 for receiving and storing digital data corresponding to the selected amplitude for the output stimulation pulses. The data content of this memory is applied by data bus 39 to a decoder 40, a decoder 41, and a switch 42.

Timing signals are provided by a reference crystal 51. Conductor 52 connects to the input of width counter 55. The count accumulated in width counter 55 is output over data bus 56 to decoder 22, and the overflow count of counter 55 is conveyed by conductor 57 to the input of rate counter 60, and also to the input of counter-decoder 30.

Flip-flop circuit 66 receives its SET input from rate counter 60 over conductor 65, and its RESET input from decoder 22 by conductor 64. A branch of conductor 65 also connects to an enable input of decoder 22. The Q output of flip-flop 66 connects through conductor 73 to one input of AND gate 70. The output of counter-decoder 30 connects over conductor 71 to another input of AND gate 70. The output of decoder 41 connects over conductor 72 to another input of AND gate 70, and conductor 16 from memory 14 connects as the remaining input to AND gate 70.

The output of AND gate 70 is connected to conductor 76, one branch of which connects to counter 80, which is labeled the pulses per step counter. Another branch of conductor 76 connects to an enable input of analog output circuit 90. The count in counter 80 is applied by data bus 81 to decoder 36, and the output of decoder 36 is connected by conductor 37 to an input of a counter 84 which is labeled the amplitude counter, and to a reset input of counter 80. The count in amplitude counter 84 is conveyed by data bus 85a to decoder 40, and by data bus 85b to switch 43. Counter 84 also receives a reset input from a branch of conductor 71. The output of decoder 40 is conveyed by conductor 86 to another input of counter 84.

Digital to analog converter 96 receives digital inputs from data bus 97, which connects from both switches 42 and 43. The analog output of converter 96 is connected by conductor 98 to the input of analog output circuit 90. Output circuit 90 provides electrical stimulating pulses at terminals 92 and 93, the latter of which is connected through capacitor 91 from output circuit 90. These stimulating pulses are carried by leads (not shown) to electrodes (not shown) to provide electrical tissue stimulation.

Figure 2:
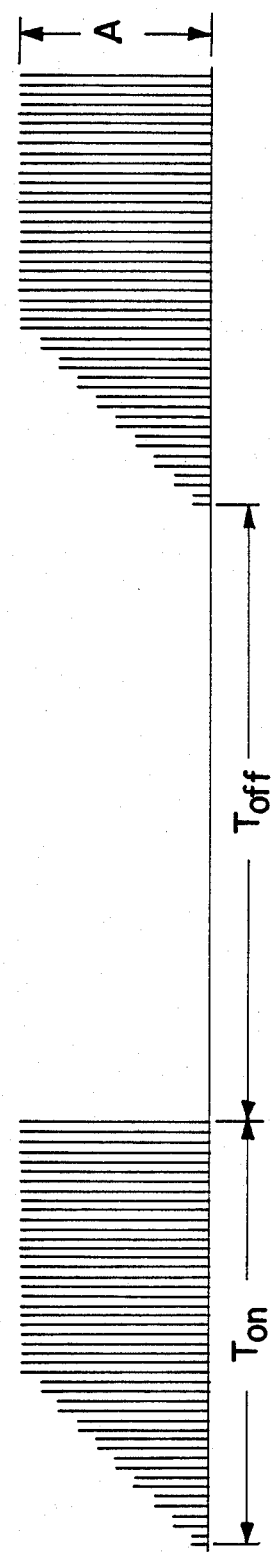
FIG. 2 is a diagram of output waveforms of the stimulator of FIG. 1.

The output produced by the embodiment of FIG. 1 in a burst or cycle mode of operation is indicated in FIG. 2, in which the vertical axis represents pulse amplitude and the horizontal axis represents time. Two groups or bursts of pulses are shown, each of which contains a number of individual pulses. The on time of the waveform of FIG. 2 is indicated by $T_{on}$, and this corresponds to the preselected program value stored in ON time of memory 28. The off time of the waveform is indicated by $T_{off}$, and this corresponds to the preselected quantity stored in OFF time memory 32. The amplitude of the pulse stimulation is indicated by A, and this corresponds to the preselected value stored in amplitude memory 38.

Figure 3:
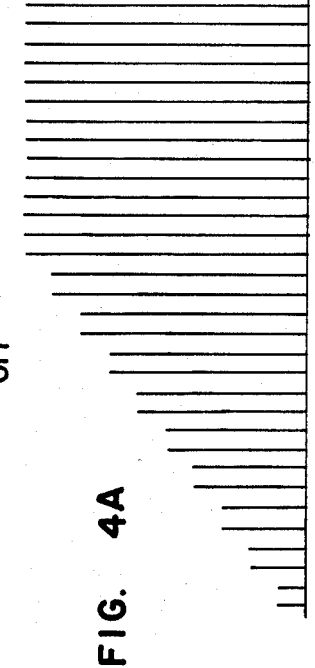
FIG. 3 is a diagram of a pair of output pulses of waveforms of FIG. 2 in expanded scale.
Figure 4A:
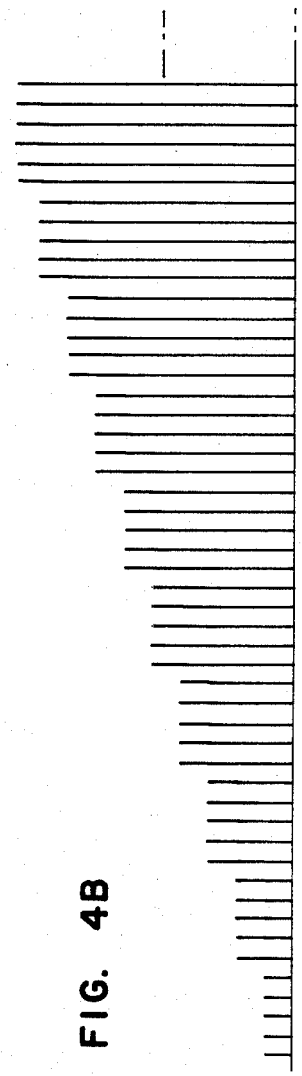
FIGS. 4A and 4B are diagrams at an expanded scale of output pulses from the stimulator of FIG. 1 illustrating the soft start feature for a group of pulses.
Figure 4B:
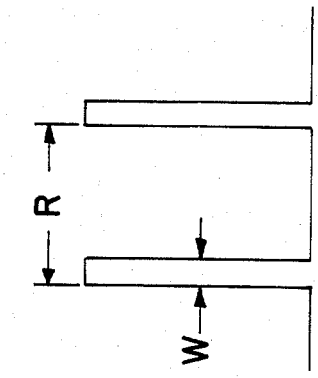

Individual pulses within a burst or group are shown at an expanded vertical and horizontal scale in FIG. 3. The letter W indicates the pulse width, which corresponds to the preselected value stored in pulse width memory 20. The pulse period is indicated by R which corresponds to the preselected quantity stored in pulse rate memory 24. The gradual turn-on or soft start is seen at the beginning of each group of pulses in FIG. 2, and is seen in greater detail in FIGS. 4A and 4B, which is shown at an expanded scale as compared with FIG. 2, but not expanded as greatly as FIG. 3. In FIGS. 4A and 4B, individual pulses are shown as individual lines, it being understood that the pulse width is typically many times smaller than the interval between successive pulses. FIG. 4A shows an increasing pulse amplitude at a slope or rate of 2 pulses per step of amplitude increase. Thus, the first two pulses are at the first amplitude increment, the next two pulses are at the next increment, and so on until the final selected amplitude would be reached. FIG. 4B shows the beginning of a group at 5 pulses per amplitude step, wherein each successive amplitude increment is repeated for 5 pulses before incrementing to the next amplitude value.

With the on-off memory 14 set to on, an ON time programmed in memory 28 and a non-zero pulse per step programmed in memory 34, the stimulator of FIG. 1 will put out groups of pulses on a recurring basis, generally of the type indicated in FIG. 2, from the stimulator output terminals 92, 93, which would of course be connected through leads to an electrode. Programming a zero value in pulse per step memory 34 will disable gradual turn-on operation, in which case all pulses in each group will be delivered at the full amplitude programmed.

For example, in a preferred embodiment, the pulse width is programmable between 0.03 and 1.92 milliseconds. The pulse rate is programmable from 1 to 256 hertz, corresponding to escape intervals from 1 second to 3.9 milliseconds. The on time is programmable from 0.06 to 64 seconds. The off time is programmable from 0.06 seconds to approximately 17 minutes. The amplitude is programmable from 0 to 9.0 volts. The soft start rate is selectable from 1 to 7 pulses per step. While the above numeric ranges are used in the preferred embodiment, they do not represent limits for the practice of the invention, because through suitable design changes, the ranges listed above could be expanded or narrowed as desired. Also, while the magnitude of output pulses is controlled in terms of voltage in the preferred embodiment, the invention may be employed equally as well to the situation where output pulses are sought to be controlled in terms of current.

The clock pulses from oscillator 51 are counted in width counter 55, which has a full count corresponding to the maximum selectable pulse width. Counter 55 continually cycles through full count and starts again, etc. with overflow pulses being provided on lead 57 which are counted in counters 30 and 60. Alternatively, clock pulses from oscillator 51 could be applied directly to counters 60 and 30 which would be designed accordingly, but the preferred technique essentially uses width counter 55 as a divider, since the pulse width is much smaller than all of the other time increments of interest in the system. The counts for rate, on time and off time are calculated in terms of multiples of the width counter maximum count in the preferred embodiment.

Pulses from lead 57 are counted in counter 60, which is preset to a count present in memory 24. When the time interval from the preceding pulse equals that selected for the selected rate, counter 60 overflows to produce an output on conductor 65 which sets flip-flop 66 and enables decoder 22. Assuming for the moment that the other inputs to AND gate 70 are at a logical 1, the setting of flip-flop 66 enables gate 70 and produces a logical 1 at conductor 76, which is applied to analog output circuit 90. Following the overflow pulse on lead 57 which set in motion the events described above, width counter 55 again begins a count, and this time decoder 22 is enabled and produces an output at conductor 64 when the count in width counter 55 reaches correspondence with the preselected pulse width from memory 20. This pulse on conductor 64 resets flip-flop 66, terminating the logical 1 signal on conductor 76.

The above process then repeats with the result that pulses are produced on lead 76 having a width corresponding to the preselected pulse width in memory 20, and occuring at a repetition rate corresponding to the rate in memory 24. These pulses, one of which is shown by waveform 77, cause analog output circuit 90 to produce output stimulation pulses. The output pulses occur at times controlled by the occurrence of pulses at conductor 76, and they last for a duration controlled by the duration of the pulses at conductor 76. However, the amplitude of the output pulses is controlled by the analog signal at conductor 98 from D to A coverter 96.

The above sequence of generating individual pulses proceeded on the assumption that an on time interval $T_{on}$ was in progress, which places an enable signal on conductor 71 to AND gate 70. During an off interval, $T_{off}$, a logical 0 is placed on conductor 71 inhibiting the production of output pulses. Counter-decoder 30 counts pulses on lead 57, and compares them to the values in ON time memory 28 or OFF time memory 32, to alternately toggle the output on conductor 71 to produce the on and off periods corresponding to the programmed on and off time intervals.

The generation of the soft start or gradual turn-on feature is as follows. At the beginning of an on time period, amplitude counter 84 is reset by a branch of conductor 71 to an initial value corresponding to the small amplitude value for the first pulse or pulses of a group. The value used for the initial increment and subsequent increments can be chosen in the design of counter 84 and D to A converter 96. A range of increment values may be used, and the preferred embodiment uses an initial increment corresponding to an output pulse amplitude of 0.25 volts. In burst or cycle mode, the content of counter 84 is applied through bus 85b, through switch 43, and data bus 97 to D to A converter 96, and it is the count in amplitude counter 84 that controls the amplitude of the output pulse. Upon the occurrence of the first pulse in a new on time period, the initial amplitude value is applied to D to A converter 96, causing analog output circuit 90 to output the first pulse at the small or lowest amplitude increment, as indicated by the first pulse in either FIG. 4A or 4B. At the same time, the occurrence of the control pulse at conductor 76 is counted at counter 80. The count in counter 80 is compared by decoder 36 to the programmed pulses per step in memory 34. If the count in counter 80 equals the preselected number of pulses per step, decoder 36 provides an output on conductor 37 that increments amplitude counter 84 to the next amplitude value, and also resets counter 80. If counter 80 has not reached the preselected number of pulses per step, then the next pulse is delivered at the same amplitude. In this manner, the amplitude is held at a given value for the preselected number of pulses, then incremented to the next value for the same number of pulses, and so on until the amplitude corresponding the selected maximum amplitude is reached. At that time, the count in amplitude counter 84 corresponds to the amplitude in memory 38, and decoder 40 provides a signal on conductor 86 to inhibit counter 84 from advancing any further. The remaining pulses of the group for that on time are at the maximum value.

In the case where burst or cycle mode is not desired, the zero value in memory 34 is sensed by decoder 26, which produces an output on conductor 45 to cause switch 42 to be enabled and switch 43 disabled, so that the preselected amplitude in memory 38 is applied directly to D to A converter 96 and all pulses are delivered at the selected value.

Decoder 41 is provided to decode the special case of a programmed 0 amplitude, in which case a logical 0 is provided on conductor 72 to inhibit the producing of output pulses.

A comparison of FIGS. 4A and 4B shows the control that can be provided over the slope or rate at which the gradual build up of amplitude of pulses within a group can be controlled. In FIG. 4A, the pulses per step was set at 2, and the circuitry of FIG. 1 permitted 2 pulses prior to incrementing the amplitude counter each time until the maximum value was reached.

What is claimed is:

1. A remotely programmable circuit for control of gradual turn-on of electrical tissue stimulation comprising:
   register means for holding digital signals corresponding to the amplitude of stimulation pulses to be delivered;
   pulse generating means responsive to said digital signals for producing electrical tissue stimulation pulses;
   means for altering said digital signals in response to successive occurrences of a predetermined number of pulses to cause discrete increases in the amplitude of stimulation pulses from the start of a stimulation interval until a predetermined maximum amplitude is obtained, said means for altering including first memory means for holding digital signals corresponding to said predetermined number, counter means for counting said pulses, and decoding circuit means responsive to said first memory means and said counter means for causing said discrete increases and for resetting said counter means when the count in said counter means corresponds to said predetermined number; and
   means for receiving and decoding remotely generated programming signals and altering the contents of said first memory means to permit the rate of increase in the amplitude of stimulation pulses to be remotely programmed.

2. A circuit according to claim 1 wherein said means for altering includes second memory means for holding digital signals corresponding to said predetermined maximum amplitude and wherein said decoding circuit means is further responsive to said second memory means and said register means for preventing the digital signals in said register means from being altered when the signals in said register means correspond to said predetermined maximum amplitude.

3. A circuit according to claim 1 or 2 wherein said register means comprises a counter.

4. A remotely programmable circuit for control of gradual turn-on of electrical tissue stimulation pulses produced by a stimulation generator, comprising:
   clocking means for producing periodic signals at a predetermined stimulation rate;
   memory means for holding digital signals corresponding to a predetermined number of periodic signals;
   counting means connected to said clocking means for maintaining digital signals corresponding to a count of said periodic signals;
   decoding circuit means connected to said memory means and said counting means for producing a pulse amplitude incrementing signal when the digital signals in said memory means and said counting means correspond;
   pulse amplitude stepping means responsive to said incrementing signal for causing said generator to increase stimulation pulse amplitude by a discrete amount and for resetting said counting means upon each increase;
   maximum amplitude control means for preventing said decoding circuit means from increasing the amplitude of the stimulation pulses above a predetermined amplitude; and
   means for receiving and decoding remotely generated programming signals and altering the contents of said memory means to permit the rate of increase in the amplitude of stimulation pulses to be remotely programmed.

5. A circuit according to claim 4 wherein said maximum amplitude control means includes amplitude memory means for holding digital signals corresponding to said predetermined amplitude and amplitude decoding circuit means connected to said amplitude memory means for preventing said amplitude stepping means from being incremented when said pulse amplitude corresponds to said predetermined amplitude.

6. A circuit according to claim 5 wherein said pulse amplitude stepping means comprises a counter.

7. A remotely programmable circuit for control of gradual turn-on of electrical tissue stimulation, comprising:
   oscillator means for producing periodic signals at a predetermined stimulation rate;
   first counting means connected to said oscillator means for counting said periodic signals;
   first memory means for holding digital signals corresponding to a predetermined number of said periodic signals;
   first decoding means connected to said first memory means and said counting means for producing a stepping signal and resetting said first counting means when the count in said first counting means corresponds to the digital signals held in said first memory means;
   second counting means clocked by said stepping signal for producing amplitude controlling digital signals corresponding to the amplitude of stimulation pulses to be delivered;
   pulse generating means responsive to said amplitude controlling signals for producing electrical tissue stimulation pulses;
   second memory means for holding digital signals corresponding to a predetermined amplitude of said tissue stimulating pulses;
   second decoding means connected to said second memory means and said second counting means for preventing the count in said second counting means from advancing when the count in said second counting means corresponds to the digital signals held in said second memory means; and
   means for receiving and decoding remotely generated programming signals and altering the content of said first and second memory means to permit the rate of increase in the amplitude of stimulation pulses and the maximum stimulation pulse amplitude to be remotely programmed.

* * * * *